United States Patent [19]

Font Freide et al.

[11] Patent Number: 4,579,996
[45] Date of Patent: Apr. 1, 1986

[54] PROCESS FOR THE PRODUCTION OF HYDROCARBONS FROM $C_1$ TO $C_4$ MONOHALOALKANES

[75] Inventors: Josephus J. H. M. Font Freide, Weybridge; David J. H. Smith, Camberley, both of England

[73] Assignee: The British Petroleum Company P.L.C., London, England

[21] Appl. No.: 752,106

[22] PCT Filed: Nov. 29, 1984

[86] PCT No.: PCT/GB84/00410
§ 371 Date: Jun. 24, 1985
§ 102(e) Date: Jun. 24, 1985

[87] PCT Pub. No.: WO85/02399
PCT Pub. Date: Jun. 6, 1985

[30] Foreign Application Priority Data

Nov. 30, 1983 [GB] United Kingdom ............... 8331982

[51] Int. Cl.$^4$ ................................................ C07C 1/00
[52] U.S. Cl. ...................................... 585/642; 585/733
[58] Field of Search ................................ 585/642, 733

[56] References Cited

U.S. PATENT DOCUMENTS

| | | | |
|---|---|---|---|
| 2,488,083 | 11/1949 | Gorin et al. | 585/642 |
| 2,658,090 | 11/1953 | Geiser et al. | 585/642 |
| 2,708,210 | 5/1955 | Sias | 585/642 |
| 3,329,730 | 7/1967 | Vives | 585/642 |
| 4,524,234 | 6/1985 | Kaiser | 585/733 |

*Primary Examiner*—Curtis R. Davis
*Attorney, Agent, or Firm*—Brooks Haidt Haffner & Delahunty

[57] ABSTRACT

A $C_1$ to $C_4$ monohaloalkane is converted to hydrocarbons having a greater number of carbon atoms than the monohaloalkane reactant, in particular to aliphatic hydrocarbons in the gasoline boiling range, by contacting the monohaloalkane at elevated temperature with a clay containing either hydrogen ions and/or metal cations introduced either by exchange and/or by deposition. Preferred as catalysts are the layered clays including stabilized pillared layered clays.

10 Claims, No Drawings

PROCESS FOR THE PRODUCTION OF HYDROCARBONS FROM $C_1$ TO $C_4$ MONOHALOALKANES

The present invention relates to a process for the conversion of $C_1$ to $C_4$ monohaloalkanes into hydrocarbons having a greater number of carbon atoms than the monohaloalkane reactant, in particular to aliphatic hydrocarbons in the gasoline boiling range.

The forecast longer-term shortage of petroleum has in recent years stimulated research into the production of chemicals and fuels from other raw materials. In particular both coal and natural gas, of which there are vast reserves, have been under consideration because both are readily converted by well established technology into a mixture of gases comprising carbon monoxide and hydrogen, conventionally referred to as synthesis gas, which in turn can be converted into methanol. Methanol is a useful intermediate for the production of valuable chemicals, for example acetic acid, ethanol, esters, acetic anhydride etc and in recent years its use has been proposed both as a gasoline blending component and as a feedstock for the production of liquid gasoline range hydrocarbons by conversion over synthetic crystalline aluminosilicate catalysts, see for example U.S. Pat. No. 4,138,442 (Mobil).

An alternative approach to the production of gasoline range hydrocarbons from natural gas, which principally comprises methane, together with ethane, propane and possibly also butane, is to convert the alkanes to their alkyl monohalides and thereafter catalytically convert these to gasoline range hydrocarbons. In U.S. Pat. No. 3,894,107 (Mobil) there is described a process for converting an aliphatic organic compound of the formula R—X where X is at least one of halogen, oxygen, sulphur or nitrogen to a product comprising a complex mixture of compounds including hydrocarbon compounds having a greater number of carbon atoms than the organic compound reactant, a higher ratio of carbon atoms to heteroatoms than the organic compound reactant and a longest carbon to carbon chain length which is longer than the longest carbon chain length of the organic compound reactant by contacting the compound of formula R—X with a crystalline aluminosilicate zeolite having a silica to alumina ratio of at least about 12 and a constraint index of about 1 to 12. It is further stated that the zeolite may be in the hydrogen form or it may be base exchanged or impregnated to contain ammonium or a metal cation complement, of which the latter may be a cation of the metals of the Groups I through VIII of the Periodic Table. All the examples illustrate the use of the zeolite in the hydrogen form and in those examples in which hydrocarbons are formed, they comprise a mixture of aliphatic and aromatic hydrocarbons. There is no example illustrating the conversion of a monohaloalkane feedstock.

We have now found that a $C_1$ to $C_4$ monohaloalkane can be converted in high selectivities to hydrocarbons having a greater number of carbon atoms than the monohaloalkane reactant, and in particular to aliphatic hydrocarbons in the gasoline boiling range, using as catalyst a clay containing either hydrogen ions and/or metal cations introduced either by exchange and/or by deposition.

Accordingly, the present invention provides a process for the conversion of a $C_1$ to $C_4$ monohaloalkane to aliphatic hydrocarbons having a greater number of carbon atoms than the monohaloalkane reactant which process comprises contacting the monohaloalkane at elevated temperature with a clay containing either hydrogen ions and/or metal cations introduced either by exchange and/or by deposition.

As regards the monohaloalkane, the halide moiety may suitably be chloride or bromide, preferably chloride and the alkyl moiety may be methyl, ethyl, propyl or butyl, preferably methyl. Alternatively mixtures of monohaloalkanes, preferably comprising a monohalomethane as the principal component of the mixture, may suitably be employed. The monohaloalkanes are preferably used in the substantially pure form but may be admixed with diluents such as carbon-containing gases, nitrogen, hydrogen, oxygen or air, or with minor amounts of their polyhalogenated analogues. Monohaloalkanes may suitably be obtained by halogenation of the corresponding paraffin or a mixture of paraffins in the form for example of natural gas. Suitable processes for selectively producing methyl or ethyl monohalides are described in our copending published UK application No. 2120249A and published European application No. 0117731.

Suitable clays for use in the process of the present invention include both amorphous clays and crystalline or paracrystalline clays as described in 'Encyclopedia of Chemical Technology' (Kirk Othmer), 3rd edition published by John Wiley and Sons, pages 190-206. Suitable crystalline and paracrystalline clays include kaolins, serpentines, smectites (montmorillonites), illites or micas, glauconite, chlorites and vermiculites, attapulgite and sepiolites. The aforesaid clays may be natural or synthetic. Of the aforesaid clays, the layered clays, that is clays having a lamellar structure with interlamellar spaces disposed between the lamellar layers, are particularly suitable. Smectites, that is montmorillonite, beidellite, nontronite, hectorite, saponite and sauconite, are a preferred class of layered clay which may be employed in the process of the invention. Layered clays are generally cation-exchangeable.

Stabilized pillared layered clays, that is layered clays in which the lamellar layers are physically separated by the provision of pillars between the layers, thereby increasing their stability under certain conditions, may be used in the process of the invention. In other respects, such as their ability to cation-exchange exchangeable cations, the pillared clays are similar to their non-pillared counterparts.

Stabilised pillard layered clays which, after exchange with or deposition thereon of hydrogen ions or metal cations, are suitable for use in the process of the invention include those described in U.S. Pat. Nos. 4,176,090; 4,248,739 and 4,216,188, our copending European application publication No. 0130055 and our copending unpublished UK application Nos. 8400271, and 8333614, the disclosures of which are incorporated herein by reference.

U.S. Pat. No. 4,176,090 describes and claims an interlayered smectite clay product which includes an inorganic oxide selected from the group consisting of alumina, zirconia and mixtures thereof between the layers thereof, and which possesses an interlayer distance of from about 6 to 16 Angstroms, said interlayered clay having greater than about 50 percent of its surface area in pores of less than 30 Angstroms in diameter. Such clays can be produced by (a) reacting a smectite with a mixture of a polymeric cationic hydroxy inorganic metal complex selected from the group comprising aluminium and zirconium complexes and mixtures thereof and water to obtain a smectite having greater than 50 percent of its surface area in pores of less than 30 Angstroms in diameter after dehydration; and (b) separating the interlayered smectite from the mixture.

An improvement in this method of preparation is described in U.S. Pat. No. 4,248,739 whereby the smectite is reacted with a high molecular weight cationic hydroxy metal complex and copolymers thereof having a molecular weight of from about 2000 to 20,000. U.S. Pat. No. 4,216,188 discloses a process for the production of molecular sieves which comprises reacting a colloidal solution of a monoionic montmorillonite having a concentration of 100 mg to 800 mg montmorillonite per liter, in the form of fully dispersed negatively charged unit layers at room temperature, with an aged sol of a metal hydroxide aged for at least 5 days at ambient temperature, said metal hydroxide being selected from the group consisting of aluminium hydroxide and chromium hydroxide, at a pH adjusted below the zero charge point having a residual net positive charge on the said metal hydroxide, under vigorous agitation, resulting in a rapid flocculation of the montmorillonite cross-linked with said metal hydroxide, separating the product from the liquid phase, and stabilizing the product by heat treatment.

Our European application publication No. 0130055 describes a stabilized pillared layered clay wherein the layers are separated by the residue of a material which has reacted with hydroxyl groups associated with the clay structure. Particularly suitable residues are Lewis acids, such as magnesia or boria. Other forms of stabilised pillared layered clays may also be used.

UK patent application No. 8400271 relates to a method of treatment of a layered clay for the purpose of increasing its silicon content which method comprises hydrolysing a hydrolysable silicon compound in the presence of the layered clay. The clay so-treated is a preferred clay for use in the process of the invention because the catalyst so-treated is less prone to decay than the untreated catalyst.

UK patent application No. 8333614 relates to a pillared clay having beryllium-containing pillars which may be produced by in a first step hydrolysing a compound of beryllium and thereafter cation-exchanging a cation-exchangeable layered clay with the hydrolysate so-obtained.

The aforementioned layered clays and stabilised pillared layered clays will almost certainly contain cations associated with their layered structure, for example they may contain either alkali metal and/or alkaline earth metal cations, organic nitrogen cations or ammonium cations and possibly also organic acids or bases present in the interlamellar spaces and on available surfaces. These are generally cations which do not give rise to the most active catalysts. Consequently, in order to produce catalysts which are more active in the process of the present invention it is necessary either to exchange some or all the exchangeable cations of the clay with hydrogen ions and/or metal cations. Alternatively, the clay whether it be a layered clay, a stabilised pillared layered clay, or any other clay, may have deposited thereon either hydrogen ions or metal cations. Metal cations which may be exchanged or deposited on the clay are those of one or more metals of Groups I through VIII of the Periodic Table, of which those metals capable of forming an amphoteric oxide, for example beryllium, titanium, zirconium, hafnium, iron, cobalt, rhodium, silver, gold, zinc, aluminium, gallium, indium, silicon, germanium, tin, lead, pollonium and uranium, as well as copper are preferred. Cation-exchange may be accomplished using conventional ion-exchange techniques. Deposition of the desired metal may be accomplished by impregnation or precipitation, or by any other technique known in the art. Deposition is preferably effected by impregnation with a solution of a suitable metal compound, for example a salt of the desired metal, which almost inevitably is accompanied by exchange of exchangeable cations with cations of the desired metal. Using cation-exchange, it is preferred to exchange substantially all the exchangeable cations with cations of the desired metal. Using deposition the amount of desired metal deposited may suitably be up to 25% w/w, preferably from 0.1 to 15% w/w calculated as metal and based on the total weight of the catalyst.

Before use as a catalyst in the process of the present invention it is preferred to wash the hydrogen ion or metal-containing clay, suitably with water, and dry it by heating, suitably at a temperature up to 250° C. in either air, oxygen, an inert gas or hydrogen atmosphere, or a combination thereof.

The process for the conversion of the monohaloalkane to hydrocarbons may suitably be effected at an elevated temperature in the range from 50° to 450° C., in the case of monohalomethane preferably from 150° to 380° C. Using monohalo-ethane or-propane either individually or as major components of the feed, the preferred temperatures may be lower. The pressure may suitably be atmospheric pressure, though higher and lower pressures may be employed if desired.

The catalyst may be situated inside a reactor in the form of a fixed bed or a fluidised bed. Heat may be supplied to the reactor in whole or in part by the reaction processes occurring within the reactor. Supplemental heat may be supplied if desired by an external source, for example by means of an electric furnace.

Although the process may be operated batchwise, it is preferably operated in a continuous manner. The gas hourly space velocity (GHSV) defined as the volume of reactant gas at STP per volume of catalyst per hour for continuous operation may suitably be in the range from 1 to $10^4$ vol/vol/hour, preferably in the range from 10 to 2000 vol/vol/hour.

The process of the invention can produce aliphatic hydrocarbons in the $C_2$ to $C_{24}$ range at high selectivities depending on the nature of the monohaloalkane(s) fed, a particular characteristic of the product being that it is rich in branched-chain paraffins, thus rendering it suitable for use as a fuel or fuels supplement for use in spark ignition internal combustion engines. Moreover, such products are transportable from remote locations in admixture with crude oil.

The process of the invention will now be illustrated further by reference to the following examples.

PREPARATION OF CATALYSTS (i) Preparation of stabilised pillared layered clay (A)

Chlorhydrol (100 g, 50% w/w in water obtained from Armour Reheis) in 2 liters of distilled water was vigorously stirred whilst 100 g Wyoming bentonite powder was slowly added into the vortex of the solution. The pH of the mixture was adjusted to 5.0 by the addition of dilute ammonia solution. The mixture was then heated and stirred at 65° C. for 1 hour whilst maintaining the pH at 5.

On cooling, the clay was removed from solution by centrifuging and was washed with 3 liters of distilled water. The clay was then mixed with a further 3 liters of water, vigorously stirred for ½ hour and recentrifuged. The clay was oven dried at 80° C. and then heated at 500° C. for 2 hours. The basal $d_{001}$ spacing was 18.2 A.

(ii) Preparation of hydrogen ion-exchanged pillared layered clay (B)

10 g of pillared clay of 100 mesh, prepared as in (i) above, was added to 60 g of a 1M potassium hydroxide solution and left overnight at 80° C. The clay was filtered, washed in distilled water and refiltered to remove all extraneous ions, and added to 60 g of 1M sulphuric acid solution and left overnight. The hydrogen ion-exchanged pillared clay was filtered, washed in excess distilled water and refiltered to remove all extraneous ions and dried at 80° C. overnight.

(iii) Preparation of metal cation-exchanged pillared layered clay (C)

The preparation (ii) was repeated using 1M solutions of salts of the metals (a) gallium, (b) copper, (c) magnesium, (d) zinc and (e) caesium.

(iv) Preparation of metal cation-exchanged layered clay (D)

Finally divided sodium bentonite was cation exchanged with 0.5M aqueous solutions of appropriate salts for periods of approximately 24 hours, the aluminium salt employed was $Al_2(SO_4)_3.16H_2O$. The solutions were mechanically stirred during the first 2 hours of a period of 24 hours, after which the solid was washed repeatedly with deionised water until the excess cations had been removed. Surplus liquid was removed from the solid using a teat-pipette prior to drying in a vacuum oven at 60° C. When the clay was visibly dry it was ground until it passed 140 BSS mesh sieve. The cation-exchanged clay was then equilibrated over granular anhydrous calcium chloride in a dessicator for a minimum period of 24 hours.

(v) Preparation of silanised pillared layered clay (E)

(a) Preparation of stabilised pillared layered clay

Wyoming montmorillonite (1143 g) was added to a stirred suspension of CHLORHYDROL(RTM)(1143 g) solution in water (20 liters). The pH of the solution was adjusted to pH 5.5 with aqueous ammonia and maintained at this pH while the mixture was heated for 1 hour at 65° C. The stabilised pillared clay obtained was separated by decantation. It was washed with water, dried at 80°–100° C. and calcined at 400°–500° C. in air.

The silicon:aluminium ratio of the product was 1.33:1 by weight and the basal $d_{001}$ spacing was 17.8 Angstroms.

(b) Silanisation of stabilised pillared layered clay

The stabilized pillared layered clay (16 g) obtained in (a) above was added to a glass flask containing tetraethoxysilane (20 g). Water (40 ml) was added rapidly with vigorous stirring and the contents were maintained at about 70° C. for 1 hour. The product was separated by decantation, dried in an oven at 100° C. and calcined at 400° C. for 4 hours.

The silicon:aluminium ratio of the product was 2.8:1 and the basal $d_{001}$ spacing was 17.7 Angstroms.

(vi) Preparation of hydrogen ion-exchanged silanised pillared layered clay (F)

The procedure of (ii) above was repeated using the silanised pillared layered clay (E) in place of the stabilised pillared layered clay (A).

(vii) Preparation of metal cation-exchanged silanised pillared layered clay (G)

The procedure of (iii) above was repeated using the silanised pillared layered clay (E) in place of the stabilised pillared layered clay (A).

EXAMPLES 1 TO 3

Methyl chloride was supplied continuously to a reactor which contained the metal cation-exchanged pillared layered clay (C), the metal ion being specified in the accompanying Table 1 under the appropriate Example. The reactor was heated externally by means of an electric furnace and the heated zone was maintained at the disclosed temperature, cf Table 1. The applied GHSVs per hour units are shown in Table 1. The gaseous product stream was analysed by on-line gas chromatography.

The composition of the gaseous product streams, excluding unreacted reactants and hydrogen chloride are shown in Table 1, together with the respective monochloromethane conversions.

EXAMPLE 4

The experiment was repeated as according to Examples 1 to 3, but this time the hydrogen form (B) of the clay was used. The reactor was heated externally by means of an electric furnace and the heated zone was maintained at 600K. The applied GHSV is shown in Table 1.

The composition of the gaseous product stream, excluding unreacted reactants and hydrogen chloride is shown in Table 1. The observed monochloromethane conversion was 31%.

EXAMPLE 5

The example was repeated as according to Example 4, but his time the zinc-exchanged clay (C) was used. The GHSV used is shown in Table 1.

The composition of the gaseous product stream, excluding unreacted reactants and hydrogen chloride is shown in Table 1. The monochloromethane conversion observed was 33%.

EXAMPLE 6

The procedure of Example 1 was repeated but this time a caesium-exchanged pillared layered clay (C) was used.

The conditions and composition of the gaseous product stream are shown in Table 1.

EXAMPLE 7

The procedure of Example 1 was repeated using in place of the metal-cation exchanged pillared layered clay the aluminium-exchanged layered clay (D).

The conditions and composition of the gaseous product stream are shown in Table 1.

EXAMPLE 8

The procedure of Example 1 was repeated using the hydrogen ion-exchange silanised pillared layered clay (F) in place of the metal cation-exchanged pillared layered clay.

EXAMPLES 9 AND 10

The procedure of Example 1 was repeated using the metal cation-exchanged silanised pillared layered clay (G) in place of the stabilised pillared layered clay (A). The nature of the metal cation is shown in Table 2.

The composition of the gaseous product stream, excluding unreacted reactants and hydrogen chloride, is shown in Table 2.

TABLE 1

Gaseous Hydrocarbon Product Stream Distribution (% v/v), Excluding Unreacted Reactant and Hydrogen Chloride, Using Monochloromethane Over Clays

| COMPOUND | 1 | 2 | 3 | 4 | 5 | 6 | 7 |
|---|---|---|---|---|---|---|---|
| methane | 13 | 8 | 40 | 26 | 13 | 95 | 23 |
| ethylene | 20 | 25 | 29 | 27 | 26 | 3 | — |
| ethane | 2 | — | 1 | — | — | 1 | 30 |
| propylene | — | — | — | 6 | — | 1 | — |
| propane | — | 13 | — | 6 | 12 | tr | 15 |
| i-butane | 65 | 36 | 26 | 24 | 33 | — | 26 |
| n-butane | tr | 2 | 4 | 1 | 1 | — | tr |
| butenes | — | — | — | — | — | — | — |
| i-pentane | tr | 12 | — | 8 | 11 | — | 6 |
| n-pentane | tr | — | — | tr | — | — | — |
| pentanes | — | — | — | — | — | — | — |
| i-hexanes | tr | — | — | 1 | — | — | — |
| n-hexane | — | — | — | 1 | — | — | — |
| heptanes | — | — | — | — | — | — | — |
| benzene | — | — | — | — | — | — | — |
| toluene | — | — | — | — | — | — | — |
| ethyl chloride | tr | 4 | — | — | 3 | — | — |
| ion-exchanged clay | Gallium | Copper | Magnesium | Hydrogen | Zinc | Caesium | Aluminium |
| Temperature/K. | 650 | 600 | 650 | 600 | 600 | 650 | 600 |
| GHSV/h$^{-1}$ | 66 | 59 | 64 | 68 | 74 | 90 | 30 |
| Monochloromethane Conversion to Gaseous Hydrocarbon Products | 44 | 39 | 5 | 31 | 33 | 7 | 9 |

TABLE 2

Gaseous Hydrocarbon Product Stream Distribution (% v/v), Excluding Unreacted Reactant and Hydrogen Chloride, Using Monochloromethane Over Silanised Pillared Layered Clays

| Compound | 8 | 9 | 10 |
|---|---|---|---|
| methane | 6 | 7 | 6 |
| ethylene | 14 | 18 | 29 |
| ethane | tr | tr | 1 |
| propylene | 46 | — | — |
| propane | 7 | 17 | 16 |
| i-butane | 1 | 44 | 35 |
| n-butane | tr | 2 | 2 |
| butenes | 20 | 4 | 1 |
| i-pentane | tr | 9 | 10 |
| n-pentane | 5 | — | — |
| pentenes | — | — | — |
| i-hexanes | — | — | — |
| n-hexane | — | — | — |
| heptanes | — | — | — |
| benzene | — | — | — |
| toluene | — | — | — |
| ethyl chloride | — | — | — |
| ion-exchanged clay | H | Ga | Zn |
| Temperature/°K. | 600 | 600 | 600 |
| GHSV/h$^{-1}$ | 200 | 50 | 50 |
| Monochloromethane Conversion to Gaseous Hydrocarbon Products | 32 | 36 | 37 |

We claim:

1. A process for the conversion of a $C_1$ to $C_4$ monohaloalkane to aliphatic hydrocarbons having a greater number of carbon atoms than the monohaloalkane reactant which process comprises contacting the monohaloalkane at elevated temperature with a clay containing either hydrogen ions and/or metal cations introduced either by exchange and/or by deposition.

2. A process according to claim 1 wherein the clay is a layered clay.

3. A process according to claim 2 wherein the layered clay is a smectite.

4. A process according to claim 2 wherein the layered clay is a stabilised pillared layered clay.

5. A process according to claim 4 wherein the layers are separated by the residue of a material which has reacted with hydroxyl groups associated with the clay structure.

6. A process according to claim 5 wherein the residue is a Lewis acid.

7. A process according to claim 2 wherein the layered clay is one which has been treated for the purpose of increasing its silicon content by hydrolysing a hydrolysable silicon compound in its presence.

8. A process according to claim 4 wherein the stabilised pillared layered clay has beryllium-containing pillars.

9. A process according to claim 1, 2, 3, 4, 5, 6, 7 or 8 wherein the clay contains either hydrogen ions or cations of at least one of the metals gallium, copper or zinc.

10. A process according to claim 9 wherein the monohaloalkane is monochloromethane and the elevated temperature is in the range from 150° to 380° C.

UNITED STATES PATENT AND TRADEMARK OFFICE
CERTIFICATE OF CORRECTION

PATENT NO. : 4,579,996
DATED : April 1, 1986
INVENTOR(S) : JOSEPHUS J.H.M. FONT FREIDE and DAVID J.H. SMITH It is certified that error appears in the above-identified patent and that said Letters Patent are hereby corrected as shown below:

Col. 1, line 41, "heteratoms" should read --heteroatoms--

Col. 6, line 45, "his time" should read --this time--

Signed and Sealed this

First Day of July 1986

[SEAL]

Attest:

DONALD J. QUIGG

Attesting Officer

Commissioner of Patents and Trademarks